US008630467B2

(12) United States Patent
Masumoto

(10) Patent No.: US 8,630,467 B2
(45) Date of Patent: Jan. 14, 2014

(54) DIAGNOSIS ASSISTING SYSTEM USING THREE DIMENSIONAL IMAGE DATA, COMPUTER READABLE RECORDING MEDIUM HAVING A RELATED DIAGNOSIS ASSISTING PROGRAM RECORDED THEREON, AND RELATED DIAGNOSIS ASSISTING METHOD

(75) Inventor: Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 339 days.

(21) Appl. No.: 12/894,940

(22) Filed: Sep. 30, 2010

(65) Prior Publication Data

US 2011/0075900 A1 Mar. 31, 2011

(30) Foreign Application Priority Data

Sep. 30, 2009 (JP) ................................. 2009-226217
Mar. 31, 2010 (JP) ................................. 2010-080957

(51) Int. Cl.
*G06K 9/00* (2006.01)

(52) U.S. Cl.
USPC ........................................................ 382/128

(58) Field of Classification Search
None
See application file for complete search history.

(56) References Cited

U.S. PATENT DOCUMENTS

| 5,865,752 | A | * | 2/1999 | Seyed-Bolorforosh et al. ............................ 600/454 |
| 5,987,345 | A | * | 11/1999 | Engelmann et al. .......... 600/407 |
| 7,620,229 | B2 | | 11/2009 | Oosawa |
| 7,646,903 | B2 | | 1/2010 | Kaftan et al. |
| 7,903,860 | B2 | * | 3/2011 | Grasruck et al. .............. 382/132 |
| 8,068,647 | B2 | * | 11/2011 | Lin ................................ 382/128 |
| 2002/0102014 | A1 | * | 8/2002 | Ozaki et al. .................... 382/132 |
| 2005/0036689 | A1 | * | 2/2005 | Mahdavieh .................... 382/199 |
| 2005/0113961 | A1 | * | 5/2005 | Sabol et al. .................... 700/182 |
| 2005/0228242 | A1 | | 10/2005 | Kawamura et al. |
| 2007/0081701 | A1 | | 4/2007 | Sirohey et al. |
| 2007/0118399 | A1 | | 5/2007 | Avinash et al. |
| 2008/0101665 | A1 | * | 5/2008 | Collins et al. ................. 382/128 |
| 2008/0242977 | A1 | | 10/2008 | Sirohey et al. |
| 2008/0292174 | A1 | * | 11/2008 | Sato .............................. 382/132 |
| 2010/0250275 | A1 | | 9/2010 | Sakagawa et al. |
| 2011/0075900 | A1 | * | 3/2011 | Masumoto .................... 382/128 |

FOREIGN PATENT DOCUMENTS

| JP | 2001137230 | A | 5/2001 |
| JP | 2005319283 | A | 11/2005 |
| JP | 2006-167287 | A | 6/2006 |
| JP | 2007280229 | A | 10/2007 |

(Continued)

OTHER PUBLICATIONS

Office Action dated Feb. 2, 2012, issued in corresponding European Application 10180843.4.

(Continued)

*Primary Examiner* — Andrew W Johns
*Assistant Examiner* — Tahmina Ansari
(74) *Attorney, Agent, or Firm* — Sughrue Mion, PLLC

(57) ABSTRACT

A plurality of sets of volume data obtained by imaging a subject on different imaging dates or different imaging times are analyzed, to calculate at least one type of index value that represents the state of the subject within each set of volume data. Transition data that represent transitions in the index values are generated for each type of index value, based on the calculated index values. At least one subject map that includes a region in which transitions are detected is generated. Specified data from among the calculated index values and the generated transition data are correlated with regions within each subject map where transitions are detected, and output to a predetermined screen.

6 Claims, 12 Drawing Sheets

(56) References Cited

FOREIGN PATENT DOCUMENTS

| JP | 2009082442 A | 4/2009 |
|---|---|---|
| JP | 2009095550 A | 5/2009 |
| WO | 2009050962 A1 | 4/2009 |

OTHER PUBLICATIONS

Extended European Search Report dated Mar. 16, 2011, Appln. No. 10180843.4-2218.

Database Design and Implementaion for Quantitative Image Analysis Research, Matthew S. Brown, et al. IEEE: Transactions on Information Technology in Biomedicine, vol. 9, No. 1, Mar. 2005.

Preparation and Display of Image Data, Chapter 4, XP-002454906, Joseph V. Hajnal, 0-8493-0064-9/01; 2001.

Japanese Office Action issued Oct. 15, 2013 in corresponding Japanese Patent Application No. 2010-080957, 3 pages in Japanese and English. Partial Translation.

Japanese Office Action issued Jul. 23, 2013 in corresponding Japanese Patent Application No: 2010-080957, 5 pages in Japanese and English.

* cited by examiner

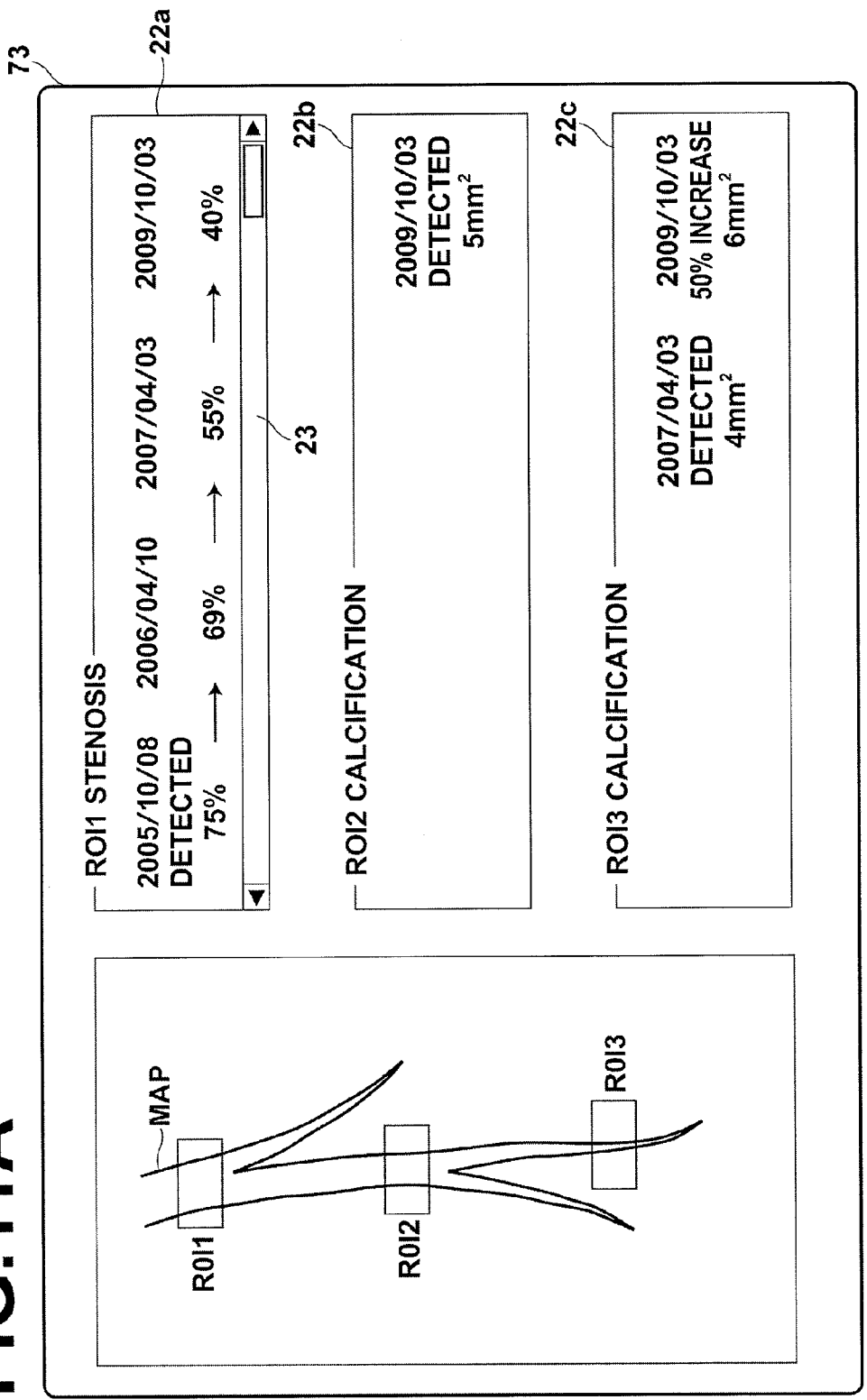

DIAGNOSIS ASSISTING SYSTEM USING THREE DIMENSIONAL IMAGE DATA, COMPUTER READABLE RECORDING MEDIUM HAVING A RELATED DIAGNOSIS ASSISTING PROGRAM RECORDED THEREON, AND RELATED DIAGNOSIS ASSISTING METHOD

BACKGROUND OF THE INVENTION

1. Field of the Invention

The present invention is suited for utilization in the medical field, and is related to a system and a method for assisting image diagnosis using three dimensional image data. The present invention is also related to a computer readable recording medium having a diagnosis assisting computer program stored thereon.

2. Description of the Related Art

In image diagnosis, there are cases in which images of a subject obtained during recent examinations (hereinafter, referred to as "current images") are compared against images of the same subject obtained in previous examinations (hereinafter, referred to as "past images"), to confirm changes in symptoms of disease (hereinafter, referred to as "comparative image observation"). A technique that generates and displays an image that represents the differences between a current image and a past image (temporal subtraction technique) is known as a technique for assisting comparative image observation. For example, U.S. Pat. No. 7,620,229 discloses an apparatus that generates and displays a subtraction image from projection images generated from three dimensional images.

In many cases, comparative image observation is performed with respect to two images. However, there are cases in which images obtained from two or more prior examinations are compared in order to confirm the progress of treatment and to consider treatment protocols. That is, there are cases in which it becomes necessary to understand stepwise changes that occur among three or more images. However, subtraction images cannot represent stepwise changes that occur among three or images in an easily understandable format.

SUMMARY OF THE INVENTION

The present invention has been developed in view of the foregoing circumstances. It is an object of the present invention to provide a system, a program, and a method that assists diagnosis and consideration of treatment protocols, by displaying temporal changes that occur in subjects in a format which can be understood with a single glance, regardless of the number of images to be compared.

A diagnosis assisting system of the present invention is a system equipped with a volume data storage means, a volume data selecting means, an index value calculating means, a map generating means, and a display control means, to be described below. In addition, a computer readable non transitory recording medium, on which a diagnosis assisting program of the present invention is recorded, causes one or a plurality of computers to function as the volume data storage means, the volume data selecting means, the index value calculating means, the map generating means, and the display control means, to be described below. The diagnosis assisting program of the present invention is constituted by a plurality of program modules. The functions of each of the aforementioned means are realized by one or a plurality of program modules. The group of program modules is provided to users by being recorded in storage media such as CD-ROM's and DVD's, by being recorded in a storage unit attached to a server computer in a downloadable state, or by being recorded in network storage in a downloadable state. A diagnosis assisting method of the present invention is a method that assists diagnosis, by causing a single computer or a plurality of computers to execute the processes of the volume data storage means, the volume data selecting means, the index value calculating means, the map generating means, and the display means, to be described later.

The volume data storage means stores a plurality of sets of volume data, obtained by imaging at least one subject a plurality of times on different imaging dates or at different imaging times, in a predetermined storage device, correlated with subject identifying data and imaging date/time data. The storage device may be an internal memory or a storage of a computer that constitutes the diagnosis assisting system, an external storage device which is connected to the computer either directly or via a network, or the like.

Note that the term "subject" refers to a target of examination, that is, a portion which is the target of imaging and diagnosis. For example, in the case that the lungs and the stomach of a single patient are examined, there are two subjects, although there is only one patient. In this case, it is preferable for the subject identifying data to include both patient data and imaged portion data.

The volume data selecting means selects a plurality of sets of volume data correlated with subject identifying data that represents a specified subject, from among the sets of volume data stored in the storage device. Thereby, a plurality of sets of volume data regarding the same subject obtained on different imaging dates/times are obtained. For example, in the case that three CT examinations are performed on a subject, three sets of volume data, each of which is obtained at each examination, are obtained.

The index value calculating means calculates at least one type of index value that represents the state of the subject within each set of volume data, by analyzing the selected plurality of sets of volume data. The transition data generating means generates transition data that represent transitions in the index values for each type of index value, based on the index values calculated for each set of volume data. For example, in the case that stenosis rates of blood vessels and the volume of calcified regions are calculated as index values, data representing transitions in stenosis rates and data representing transitions in the volume of calcified regions are both generated.

The map generating means generates at least one subject map that includes regions in which transitions are detected, by employing the transition data and at least one of the selected sets of volume data. A single subject map may be generated. Alternatively, a plurality of maps, such as a global map and detailed maps, may be generated.

The display control means outputs data specified by predetermined operations from among the index values calculated by the index value calculating means and the transition data generated by the transition data generating means to a predetermined screen, correlated with the regions on the at least one subject map at which the transitions have been detected. The data output to the screen are specified by users performing predetermined operations via selection menus, a setting screen, or the like.

According to the configuration described above, the index values and transition data which are displayed on the screen correlated with the subject map enable instantaneous understanding of temporal changes in the state of the subject. For this reason, temporal changes of the states of subjects can be known without performing comparative image observation for a great number of sets of data, even in cases that repeated examinations are performed and a great number of sets of volume data have been accumulated and stored.

The diagnosis assisting system of the present invention may further comprise: predicting means, for calculating index values that represent the future states of the subjects, based on the transition data. In this case, the display control means outputs the index values calculated by the predicting means, correlated with the regions on the at least one subject map at which the transitions have been detected. The index values that represent the future states of the subjects are effective as information for determining treatment protocols.

In the configuration that comprises the predicting means, it is preferable for the diagnosis assisting system of the present invention to further comprise transition data storage means, for storing the transition data with respect to a plurality of subjects. In this case, the predicting means selects transition data similar to the transition data generated by the transition data generating means, from among the transition data stored in the transition data storage means, and calculates the index values that represent the future states of the subjects based on the similar transition data. The accuracy of predictions can be improved, by utilizing actual medical cases.

It is preferable for the diagnosis assisting system of the present invention to further comprise: region of interest setting means, for setting at least one region of interest within each of the selected sets of volume data. In this case, the index value calculating means outputs index values that represent the states of the regions of interest, with respect to the at least one region so interest which has been set in one of the sets of volume data. For example, in the case that index values are calculated for cross sections, the amount of data to be processed and displayed will become great, if index values are calculated for all cross sections. In contrast, if index values are output only for cross sections which have been set as regions of interest, the processing efficiency is improved. In addition, only data that requires observation are displayed on the screen, and therefore, diagnostic efficiency is also improved.

According to the diagnosis assisting system, the diagnosis assisting method, and the computer readable recording medium on which the diagnosis assisting program of the present invention is recorded, instantaneous understanding of temporal changes in the state of the subject is enabled, even in cases that repeated examinations are performed and a great number of sets of volume data have been accumulated and stored.

BRIEF DESCRIPTION OF THE DRAWINGS

FIG. 11A is a diagram that illustrates an example of a history screen (in the case that diagnosis of coronary arteries is assisted).

DESCRIPTION OF THE PREFERRED EMBODIMENTS

Figure 1:
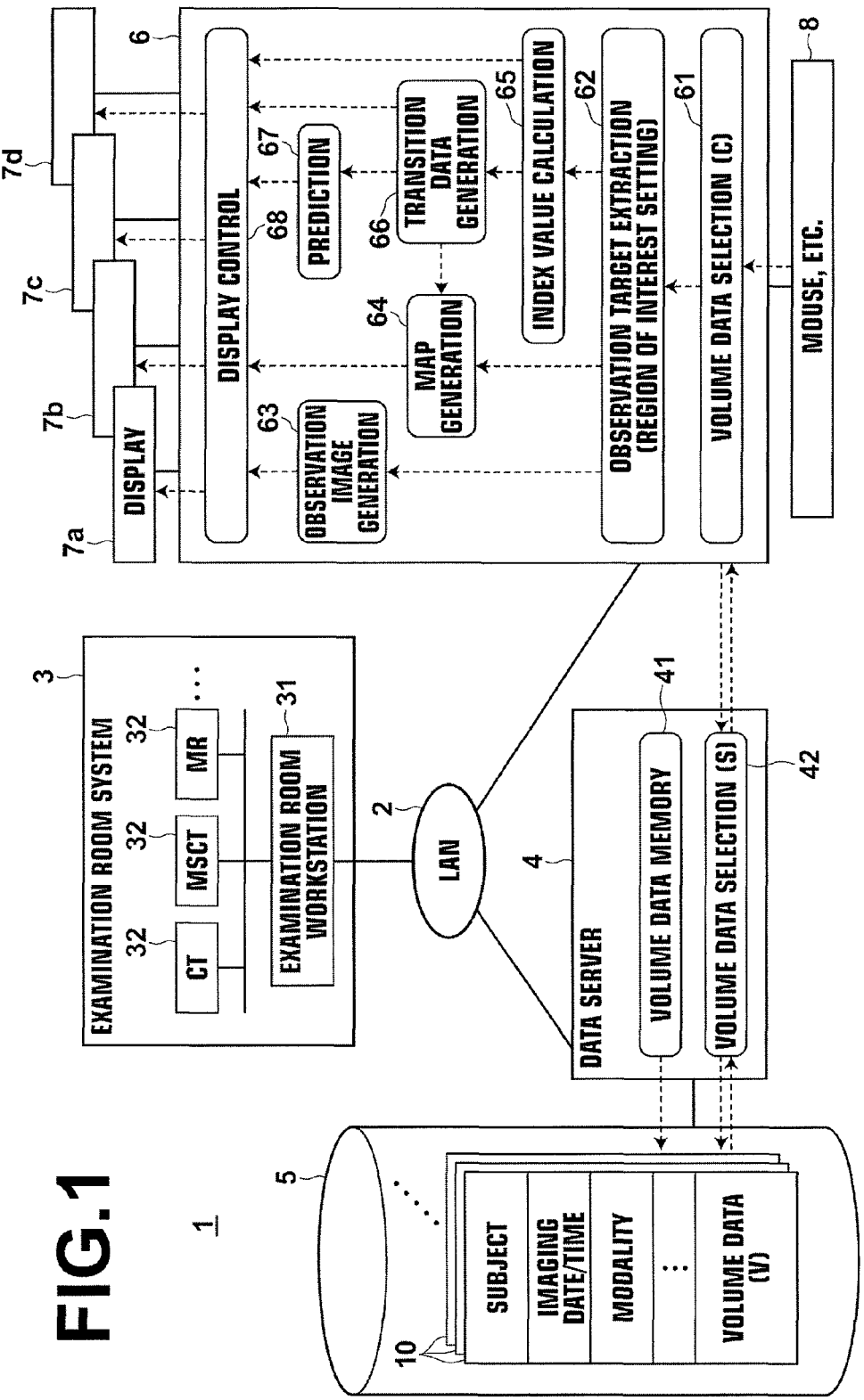
FIG. 1 is a diagram that illustrates the schematic structure of a diagnosis assisting system according to an embodiment of the present invention.

FIG. 1 illustrates the schematic structure of a diagnosis assisting system according to an embodiment of the present invention. The diagnosis assisting system of the present embodiment is constituted by: an examination room system 3; a data server 4; and a diagnosis workstation (WS 6); which are connected to each other via a local area network 2 (LAN 2).

The examination room system 3 is constituted by: a modality group 32 for imaging subjects; and an examination room workstation 31 (WS 31) for confirming and adjusting images output from each modality.

In the case that the modality 32 is that which outputs two dimensional slice data (such as a CT (Computed Tomography) apparatus and an MR (Magnetic Resonance) apparatus), the examination room WS 31 reconstructs the groups of slice data to generate three dimensional volume data, and sends the generated volume data to the data server 4 along with appended data. In the case that the modality 32 is that which directly outputs volume data (such as a MS (Multi Slice) CT apparatus and a cone beam CT apparatus), the examination room WS 31 sends the volume data to the data server 4 along with appended data.

The data server 4 is a comparatively high processing performance computer equipped with a high performance processor and a high capacity memory, in which a software program that provides the functions of a DBMS (Database Management Server) is installed. The program is stored in a storage, loaded into the memory when the computer is booted up, and executed by the processor. Thereby, the data server 4 functions as a volume data storage means 41 and as a volume data selecting means 42 on a server side (S).

The volume data storage means 41 causes the volume data and the appended data sent from the examination room WS 31 to be stored in a high capacity storage, which is connected to the data server 4, as files 10. Each of the files 10 includes a header region and a region in which the volume data are stored. The appended data which are sent from the examination room WS 31, and appended data to be used for data searching which the data server 4 adds are stored in the header region. For example, data that represent a patient ID number, name, age, sex, and imaged portions (head, chest, abdomen) are stored as data that specify subjects. In addition, data regarding the dates on which imaging was performed, and data regarding the times at which imaging was performed are stored as data that specify imaging dates/times. Further, data regarding the modality which was utilized for imaging, data regarding imaging conditions (whether an imaging agent was used, the pigment which was used, the radionuclide, the radiation dosage, etc.) are stored.

Note that the volume data which are stored in the high capacity storage 5 as files may be volume data output from imaging modalities as they are, or volume data obtained by reconstituting data (such as slice data) output from imaging modalities. Further, the volume data which are stored in the high capacity storage 5 may be volume data which has been processed, such as to remove data unnecessary for diagnosis from the volume data obtained by imaging.

The volume data selecting means 42 selects files that satisfy search conditions from among the plurality of files stored in the high capacity storage 5, in response to search requests from the diagnosis WS 6. Then, the volume data selecting means 42 sends the selected files to the diagnosis WS 6.

The diagnosis WS 6 is a general purpose workstation equipped with a normal processor and memory, in which programs that provide each of the functions to be described below are loaded. The programs are stored in the memory, and executed by the processor. By adopting this configuration, the diagnosis WS 6 functions as a volume data selecting means 61 on the client side (C), an observation target extracting means 62, an observation image generating means 63, a map generating means 64, an index value calculating means 65, a transition data generating means 66, a predicting means 67, and a display control means 68, as will be described later. In addition, four displays 7a, 7b, 7c, and 7d, and input devices 8 such as a keyboard and mouse are connected to the diagnosis WS 6.

Hereinafter, the functions, structure, and operations of the diagnosis WS 6 will be described further. The diagnosis WS 6 provides a variety of diagnosis assisting functions according to the type of tissue which is the target of diagnosis (organs, bones, muscles, blood vessels, etc.). The present invention is applicable regardless of the target of diagnosis. However, here, a case in which a function for assisting diagnosis of coronary arteries and a case in which a fat measuring function are selected will be described as examples.

Figure 2:
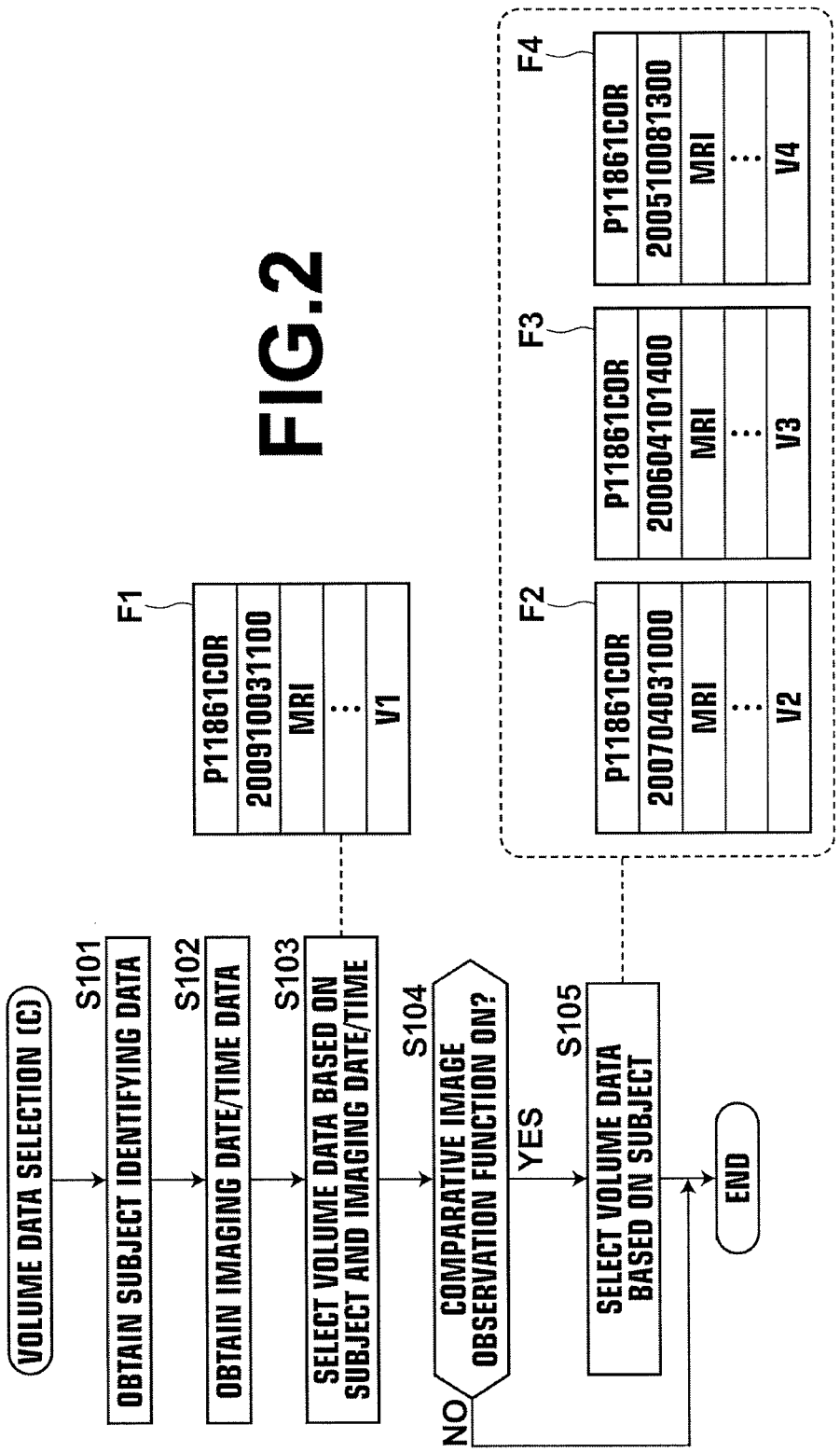
FIG. 2 is a flow chart that illustrates the steps of a process executed by a volume data selecting means (C).

FIG. 2 is a flow chart that illustrates the steps of the process performed by the volume data selecting means 61. The volume data selecting means 61 obtains subject identifying data and imaging date/time data are obtained, by detecting a function selecting operation or an operation that specifies a patient and imaging date/time performed by a user (steps S101, S102).

In the present embodiment, the subject identifying data are combinations of patient ID numbers and symbols that represent bodily portions which are targets of diagnosis. For example, in the case that the ID number of a patient is P11861 and the bodily portion is the coronary arteries represented by symbols COR, the subject identifying data is P11861COR. The patient ID number is input or selected at the initial screen. In addition, the diagnosis assisting functions provided by the present embodiment differ according to the bodily portion which is the target of diagnosis (organs, bones, muscles, blood vessels, etc.). Therefore, the bodily portion which is to be the target of diagnosis is determined by the user selecting a diagnosis assisting function. Accordingly, the subject identifying data can be obtained, by detecting the function selecting operation and an operation that specifies a patient.

In the present embodiment, the imaging date/time data is a 12 digit numerical value that represents the imaging date (year in AD, month, and day) and the imaging time (hour and minute in military time). This numerical value is input or selected by the user in the aforementioned dialog box.

Next, the volume data selecting means 61 selects volume data to be employed to generate images for observation, based on the subject identifying data and the imaging date/time data (step S103). Specifically, the subject identifying data and the imaging date/time data are sent to the volume data selecting means 42 of the data server 4, and a search is requested among the files stored in the high capacity storage 5.

Figure 7:
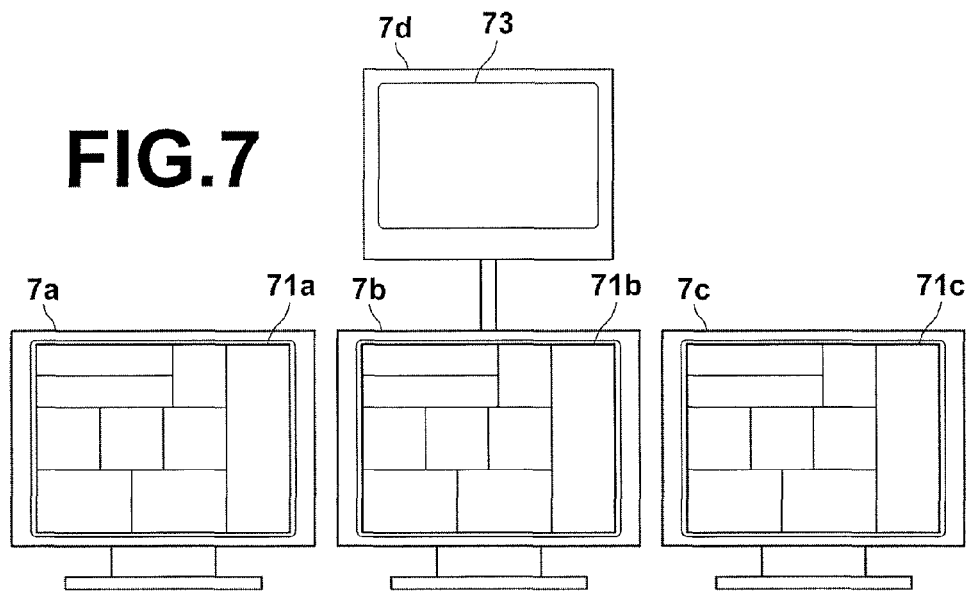
FIG. 7 is a diagram that illustrates an example of an arrangement of displays, and examples of output of diagnosis screens and history screens.

The volume data selecting means 42 selects files to which subject identifying data and imaging date/time data having the same values as the received subject identifying data and the imaging time/date data, from among the stored file groups. FIG. 7 illustrates an example in which a file F1 having subject identifying data of P11861COR, imaging date/time data of 200910031100, and modality data that represents an imaging modality of MRI is selected.

Thereafter, the volume data selecting means 61 judges whether the comparative image observation function is ON (step S104). Whether the comparative image observation function is ON may be judged by referring to setting flags stored in the memory for each function (flags that take a value of 1 when the function is ON, and take a value of 0 when the function is OFF), for example.

In the case that the comparative image reading function is ON, the volume data selecting means 61 again selects volume data sets to be employed to generate images for observation, based on the subject identifying data (step S105). The sets of volume data are selected by requesting that the volume data selecting means 42 search for files that include pertinent volume data, in a manner similar to that employed in step S103. However, in step S105, the imaging date/time data is not sent when requesting the search. Thereby, a plurality of sets of volume data regarding the specified subject and obtained on different imaging dates and times are selected.

FIG. 2 illustrates an example in which files F2, F3, and F4, having 200704031000, 200604101400, and 200510081300 appended respectively thereto as imaging date/time data are selected. Meanwhile, in the case that the comparative image observation function is OFF, the process of step S105 is not executed.

In many cases, the sets of volume data which are selected in step S105 are sets of volume data which are obtained on different examination dates, as in the example of FIG. 7. However, there are cases in which sets of volume data which are obtained at different times on the same examination date are included in the selected sets of volume data. This is because a plurality of sets of volume data are obtained during a single examination, in an examination in which a plurality of imaging operations are performed at predetermined temporal intervals following ingestion of imaging agents, for example. In addition, there are cases in which sets of volume data obtained by imaging using different modalities are selected. An example of such a case in that in which an MR apparatus is employed for periodic physical examinations, and a CT apparatus is employed for a detailed follow up examination. Further, there may be cases in which sets of volume data having a common imaging modality but different imaging methods or different imaging conditions are selected.

The observation target extracting means 62 is equipped with functions for extracting all types of body tissue from sets of volume data. The observation target extracting means 62 determines the body tissue which is to be the target of diagnosis, based on user operations or data recorded in the header regions of files supplied thereto, and selects the type of extracting process to be executed.

Figure 3:
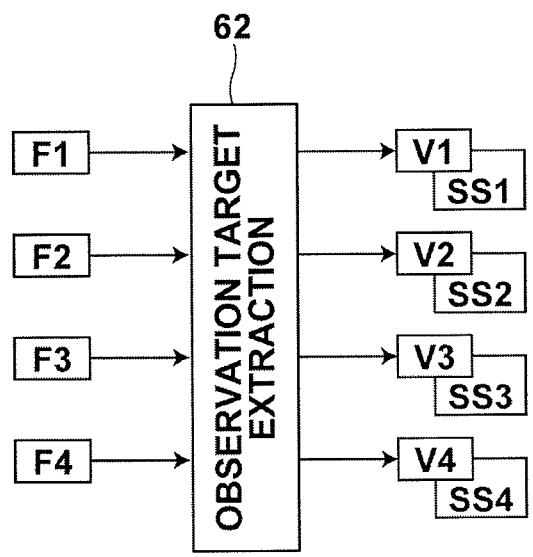
FIG. 3 is a diagram that illustrates the concept of a process executed by an observation target extracting means.

FIG. 3 illustrates an example in which the files F1 through F4 of FIG. 2 are supplied to the observation target extracting means 62. The observation target extracting means 62 extracts a region that represents an observation target from a set of volume data V1 included in the supplied file F1. Further, regions of interest are set within the extracted region either automatically or manually. Then, data that specifies the extracted region and the regions of interest are saved as a snapshot SS1 correlated with the set of volume data V1. At this time, sets of volume data and snapshots may be saved being recorded into a single file, or may be recorded into separate files and saved along with data that indicates the correlations among the files.

Note that in the present specification, a snapshot is a conglomeration of data which are obtained or generated during the process of displaying data included in a set of volume data on a diagnosis screen. In the present embodiment, the extraction results and analysis results obtained during a process for generating images for observation from sets of volume data, and further, parameters which are set in order to generate the images for observation from the sets of volume data are saved as snapshots.

In the case that a coronary artery diagnosis assisting function is selected, and data regarding use of an imaging agent, etc. are recorded in the header regions of selected files, the observation target extracting means 62 executes a process to extract a coronary artery region. Extraction of the coronary artery region is performed by employing the method disclosed in Japanese Patent Application No. 2009-069895, for example.

First, the observation target extracting means 62 extracts a region corresponding to the heart (hereinafter, referred to as "cardiac region") from each set of volume data by a predetermined algorithm. Then, a rectangular parallelepiped region that includes the cardiac region is set as a search range within the sets of volume data. Next, linear structures which are included in the search range are searched for based on a predetermined algorithm. Further, points which are estimated to be points along the cores of coronary arteries are detected, based on the linear structures detected by the search. In the following description, the points which are estimated to be points along the cores of coronary arteries will be referred to as candidate points or nodes.

The search for the linear structures is performed by calculating unique values of a 3×3 Hessian matrix for each local region within the search range. In regions that include linear structures, one of the three unique values of the Hessian matrix becomes a value close to zero, while the other two values will be relatively greater values. In addition, the unique vector that corresponds to the unique value close to zero indicates the direction of the main axis of the linear structures. In the coronary artery extracting process 14, this relationship is utilized to judge likelihoods of being linear structures based on the unique values of a Hessian matrix for each local region. In local regions in which linear structures are discriminated, the center points thereof are detected as candidate points.

Next, the candidate points which are detected by the search are linked based on a predetermined algorithm. Thereby, tree structures constituted by the candidate points and blood vessel branches (edges) that connect the candidate points are constructed. The coordinate data of the detected plurality of candidate points and vector data that represent the directions of the blood vessel branches are stored in the memory, along with identifiers for the candidate points and the blood vessel branches. Next, the shapes of the coronary arteries are discriminated in detail based on the values of the surrounding voxels (CT values) for each detected candidate point. More specifically, the outlines (the outer walls of the blood vessels) of the coronary arteries are discriminated within cross sections perpendicular to the pathways of the coronary arteries. The discrimination of shapes is performed employing a known segmentation method, such as the Graph Cuts method. Data necessary to specify the extracted coronary artery regions are generated by the above processes.

The observation target extracting means sets regions of interest, by detecting portions at which stenosis is present, calcified regions, etc. from the coronary artery regions which have been extracted as tree structures. Various methods for detecting portions at which stenosis is present and calcified regions have been proposed. An example of such a method is that which is disclosed in Japanese Unexamined Patent Publication No. 2006-167287. Note that the regions of interest may be set manually, by displaying images for observation generated by the observation image generating means 63 on a display, and by prompting users to specify the regions of interest.

Figure 4:
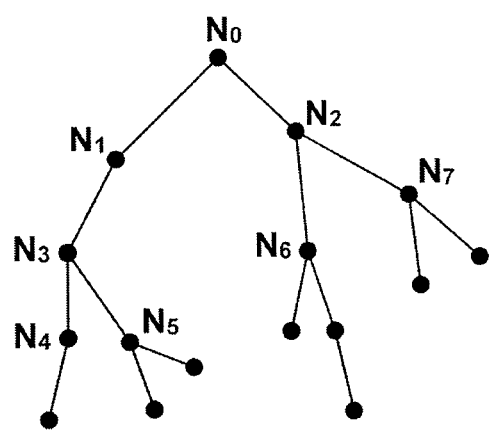
FIG. 4 is a diagram that illustrates an example of extraction results of the observation target extracting means.

After the coronary artery region is extracted and the regions of interest are set, the identifiers and the positional coordinates of the candidate points used to specify the tree structure exemplified in FIG. 4, the identifiers of each blood vessel branch and correlations among the candidate points positioned at the ends of the blood vessel branches, etc. are saved as a portion of a snapshot.

Meanwhile, in the case that a fat measuring function is selected, the observation target extracting means 62 executes a visceral fat region extracting process. Various methods for extracting visceral fat regions have been proposed. An example of such a method is that which is disclosed in Japanese Patent Application No. 2008-097630. In this method, first, a range from the vicinity of the upper edge of the liver to the vicinity of the pubic symphysis is cut out from sets of volume data obtained by imaging a target of measurement. Then, bone regions that represent bones are extracted from within axial cross sectional images obtained from within the range. Then, the boundary surfaces between the bone regions and regions toward the interiors thereof are estimated, and fat which is present toward the interior of the boundary surfaces are extracted as visceral fat regions, and fat which is present toward the exterior of the boundary surfaces are extracted as subcutaneous fat regions. Note that the fat regions and the other regions can be discriminated by the values of voxel data. In CT imaging, the signal values within fat regions are lower than those within other regions. In MRI imaging as well, the signals of fat regions can be selectively lowered, by performing imaging according to the STIR (Short TI Inversion Recovery) method.

In fat measurement, processes to detect abnormal regions are not performed, and therefore, regions of interest are not set automatically. However, in the present embodiment, users are enabled to set regions of interest manually, by performing predetermined operations with respect to images for observation which are displayed on a screen. In the case that the users set regions of interest, data that specify the regions of interest are saved as a portion of snapshots.

The observation image generating means 63 generates images for observation to be displayed on the diagnosis screen. The output of the images for observation to the display is controlled by the display control means 68. Observation formats suited for diagnosis differ according to the subjects which are the targets of diagnosis. For this reason, the types of the images for observation generated by the observation image generating means and the layout of the diagnosis screens in which the images for observation are displayed depend on the type of subject.

Figure 5A:
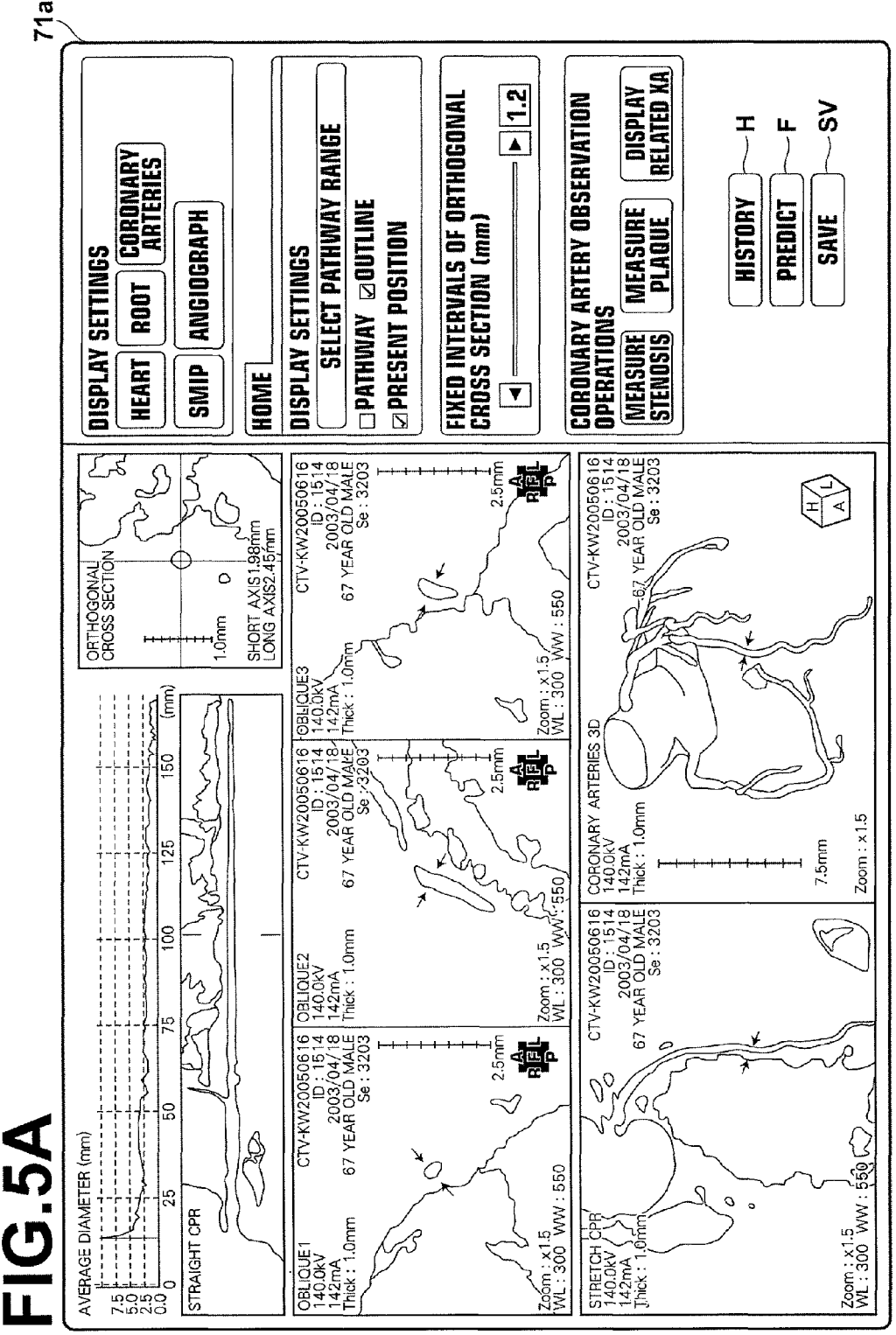
FIG. 5A is a diagram that illustrates an example of a diagnosis screen (in the case that diagnosis of coronary arteries is assisted).

For example, FIG. 5A illustrates an example of a diagnosis screen which is displayed when a function for assisting diagnosis of coronary arteries is selected. As illustrated in FIG. 5A, a straight CPR image and a stretch CPR image that represent regions of interest within the coronary arteries, four MPR images that represent an orthogonal cross section at a predetermined position within the region of interest, an axial cross section, a sagittal cross section, and a coronal cross section, and a volume rendering (3D) image that represents the entirety of the extracted coronary artery region are displayed within the diagnosis screen 71a. In addition, an operating interface that includes buttons, sliders, etc. is displayed at the right side of the diagnosis screen 71a. In the present embodiment, a history button H, a prediction button F, and a save button SV are displayed in the diagnosis screen 71a. If the save button SV is clicked, parameters that specify the images being displayed, etc., are recorded in a snapshot. If the history button H or the prediction button F is clicked, a history screen and a prediction screen, to be described later, are displayed.

Figure 5B:
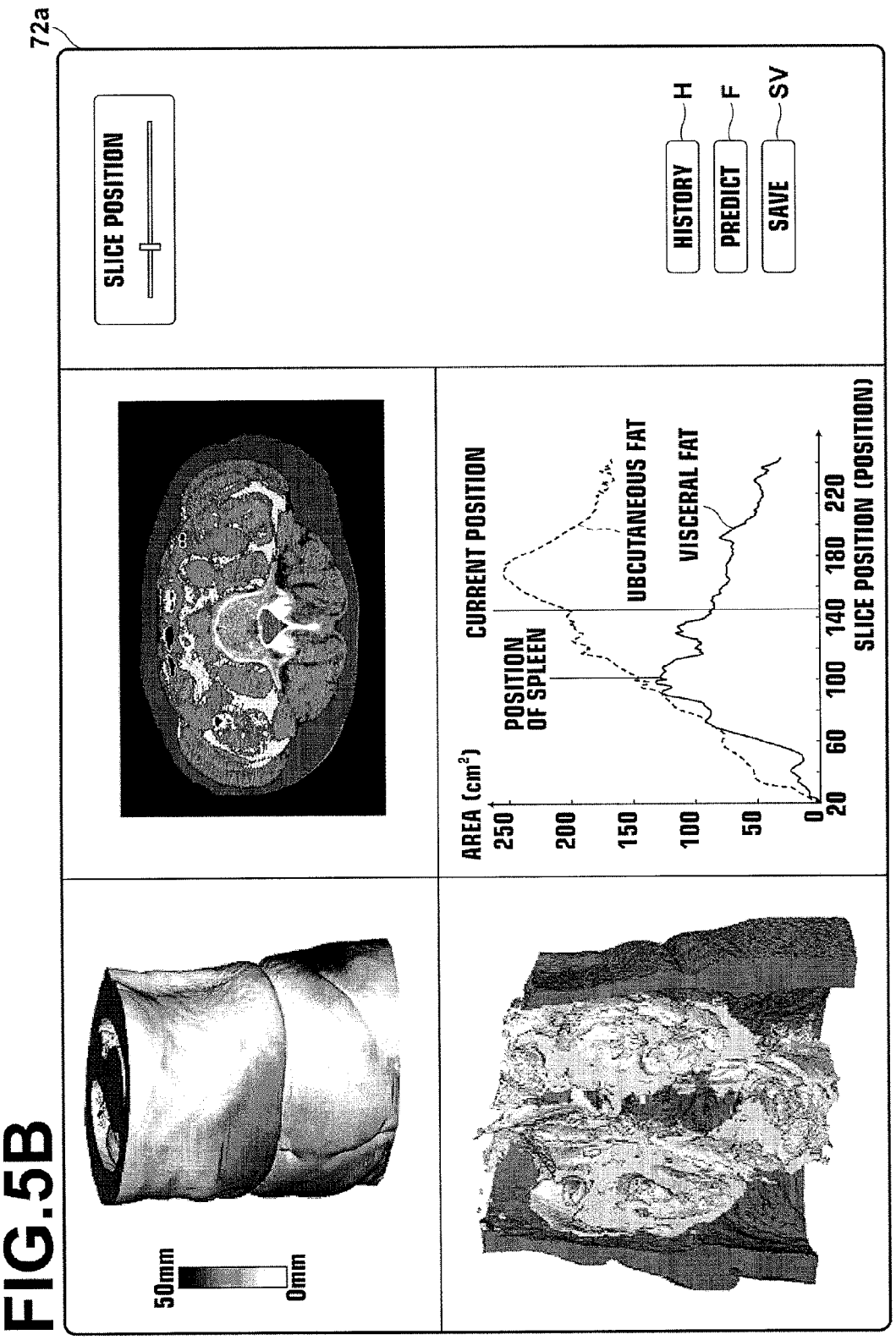
FIG. 5B is a diagram that illustrates another example of a diagnosis screen (in the case of fat measurement).

Meanwhile, FIG. 5B is a diagram that illustrates an example of a diagnosis screen which is displayed when a fat measuring function is selected. As illustrated in FIG. 5B, a volume rendering image of the entire abdomen (upper left of screen), a volume rendering image of a visceral fat region (lower left of screen), an abdominal tomographic image of a specified slice position (upper central portion of the screen), and a graph that represents the areas of visceral fat and subcutaneous fat at each slice position (lower central portion of the screen) are displayed in the diagnosis screen 72a. In addition, an operating interface is displayed at the right side of the diagnosis screen 72a. A history button H, a prediction button F, and a save button SV are displayed in the diagnosis screen 72a, in the same manner as in the diagnosis screen 71a.

Figure 6:
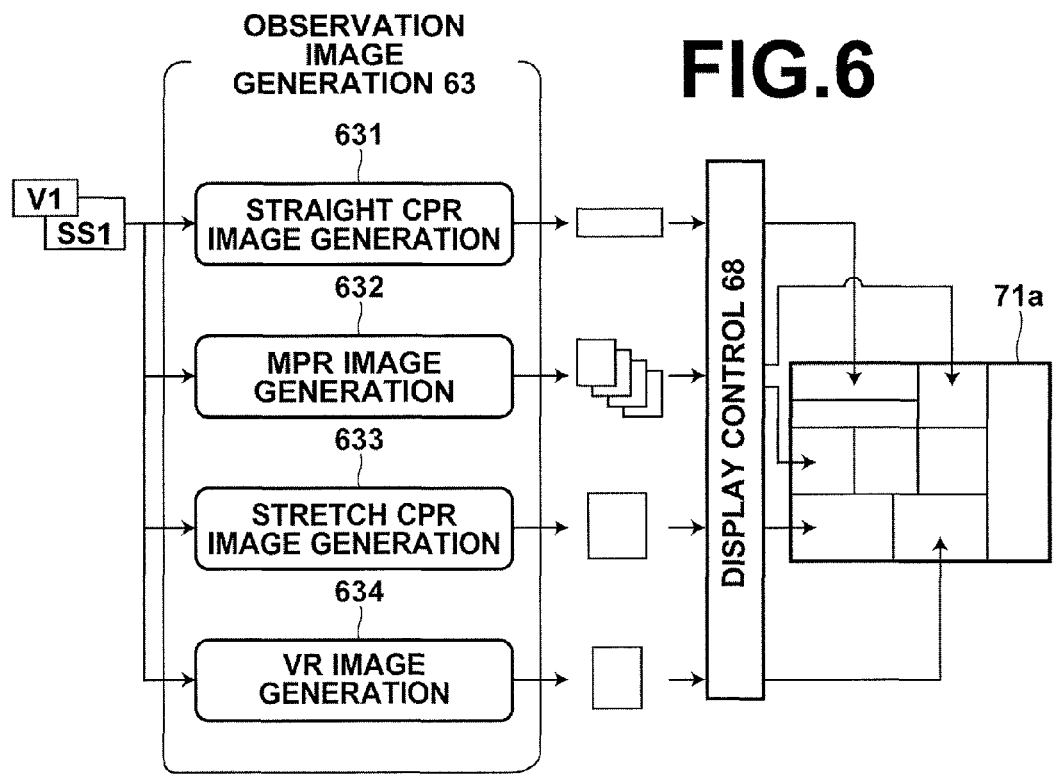
FIG. 6 is a diagram that illustrates the concepts of a process executed by an observation image generating means and a process executed by a display control means.

FIG. 6 is a diagram that illustrates the concepts of the processes executed by the observation image generating means 63 and the display control means 68 in order to display the diagnosis image 71a of FIG. 5A. The observation image generating means 63 is equipped with: a managing section (not shown) that manages the entirety of the image generating processes; a straight CPR image generating section 631; an MPR image generating section 632; a stretch CPR image generating section 633; and a VR image generating section 634. In other words, the programs that define the processes which are executed by the observation image generating means 63 include: a main program; and a plurality of program module groups that respectively define a straight CPR image generating process, an MPR image generating process, a stretch CPR image generating process, and a VR image generating process.

Note that although omitted from the figures and from the description, the observation image generating means 63 is also equipped with program modules for generating images in various other observation formats, such as MIP images, bulls eye images, and virtual endoscope images. These program modules are selectively utilized according to selected functions (targets of diagnoses).

The image generating sections 631 through 634 generate a straight CPR image, a stretch CPR image, four MPR images, and a volume rendering image as exemplified in FIG. 5A, employing the set of volume data V1 output from the observation target extracting means 62 and the snapshot SS1. Here, as methods for generating CPR images, MPR images and the like are known, and therefore, detailed descriptions of the processes executed by each of the image generating sections will be omitted. The display control means 68 arranges the images for observation generated by the observation image generating means 63 at predetermined positions (or predetermined image windows) of the diagnosis screen 71a, as illustrated in FIG. 6.

FIG. 6 only illustrates the set of volume data V1 and the snapshot SS1. However, as illustrated in FIG. 3, the observation target extracting means 62 outputs a set of volume data and a snapshot for each selected file. The observation image generating means 63 and the display control means 68 perform the same processes with respect to each combination of the sets of volume data and snapshots. Therefore, in the aforementioned example, the number of diagnosis screens constructed by the display control means 68 is four.

In the present embodiment, the display control means outputs the diagnosis screens in which the images for observation are arranged to three displays 71 through 7c from among the four displays. History screens 73 and 74 and a prediction screen 75 to be described later are output to the remaining display 7d. FIG. 7 illustrates an example in which the displays 7a through 7c, to each of which the diagnosis screens 71a, 71b, and 71c are output respectively, are arranged in a single row, and the display 7d, to which the history screen 73 to be described later is output, is provided above the central display 7b by a display arm. Note that in the example of FIG. 7, a fourth diagnosis screen which is not output (a diagnosis screen 71d for the sake of convenience in the description) may be output to any of the displays by performing a predetermined display switching operation.

Figure 8:
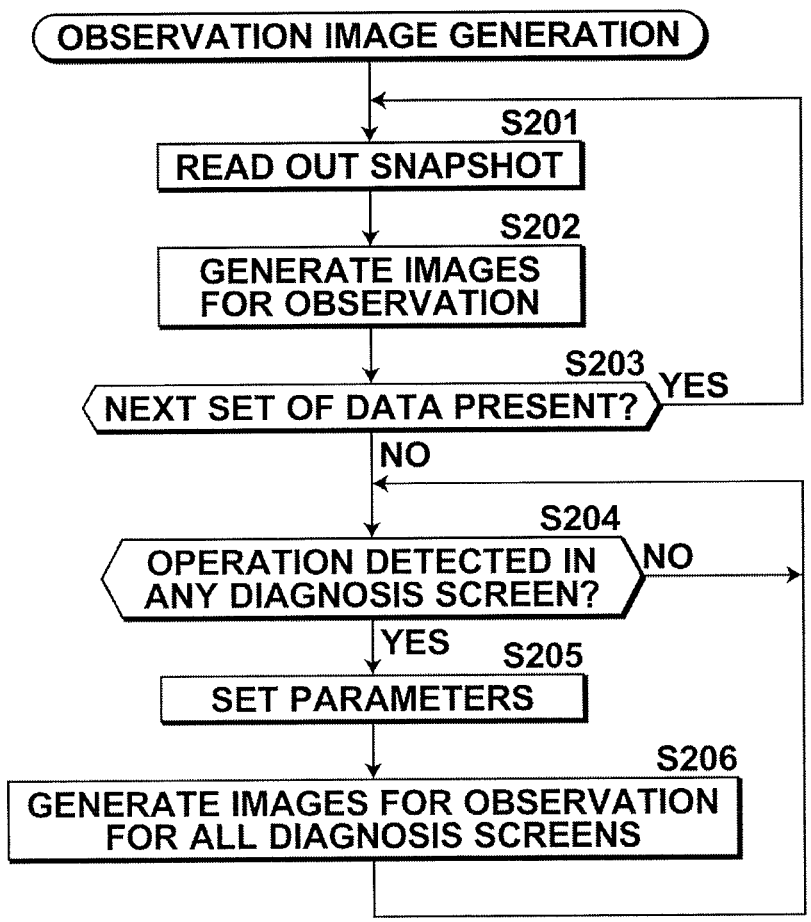
FIG. 8 is a flow chart that illustrates the steps of the observation image generating process.

FIG. 8 is a flow chart that illustrates the steps of a process executed by the main program of the observation image generating means 63. As illustrated in FIG. 6 as well, the observation image generating means 63 reads out a snapshot along with a set of volume data saved by the observation target extracting means (step S201), and generates the images for observation (step S202). In the case that there are a plurality of sets of selected volume data, and snapshots are saved for each set of volume data, the processes of steps S201 and S202 are executed with respect to a next set of volume data and a next snapshot (step S203). Thereby, a plurality of sets of images for observation that represent the states of the subject on different examination dates are generated. Each set of images for observation are output as images that constitute the diagnosis screens 71a through 71d by the display control means 68.

Here, the observation target extracting means 62 apply the same extracting algorithm and the same analyzing algorithm with respect to all of the files F1 through F4. However, because the files F1 through F4 are files obtained at different times, it is not necessarily the case that the same regions are extracted or the same regions will be automatically set as regions of interest among the files. For this reason, when the processes of steps S201 through S203 are completed, the display o the diagnosis screens 71a through 71d is not synchronized, but controlled independently. As a result, for example, the range of blood vessels which is displayed in the straight CPR image of the diagnosis screen 71a and the range of blood vessels which is displayed in the straight CPR image of the diagnosis screen 71b may differ, or the viewpoint (orientation of the image) may differ between the volume rendering image of the diagnosis screen 71a and the volume rendering image of the diagnosis screen 71b, for example.

If an operation to change the observation format of the images is performed in any of the diagnosis screens 71a through 71*d* in this state (step S204), the observation image generating means 63 resets the parameters that specify the observation formats of the images for observation, based on the detected operation (step S205). For example, the values within the groups of parameters recorded in the snapshots SS1 through SS4 are simultaneously updated in cases that operations that rotate, enlarge/reduce the sizes of images, change the slice positions of cross sections, change the orientations of cross sections, change the set regions of interest, or change the window level are performed. Thereby, common groups of parameters are recorded within updated snapshots SS1' through SS4'.

Next, the observation image generating means 63 generates images for observation for each diagnosis screen, based on the sets of volume data V1 through V4 and the updated snapshots SS1' through SS4' (step S206). In addition, if an operation that specifies a change in the layouts of diagnosis screens (such as substituting MIP images for MPR images), the images for observation which have been requested to be displayed are newly generated from the sets of volume data V1 through V4. The images for observation generated at step S206 are output simultaneously to the diagnosis screens 71*a* through 71*d* by the display control means 68. Thereby, operations which are performed with respect to a single diagnosis screen are effected on all of the diagnosis screens, and the contents of the diagnosis screens 71*a* through 71*d* which are displayed on the plurality of displays can be switched in a coordinated manner.

In addition, the contents of the changes effected by user operations are reflected in all of the snapshots in step S205. Therefore, the regions of interest, the orientations of the volume rendering images, the slice positions and orientations of the tomographic images, etc. are uniformized among all of the diagnosis screens 71*a* through 71*d*. Thereby, if operations to update the display of a single diagnosis screen are performed, the displays of the other diagnosis screens are updated in a coordinated manner.

Next, the index value calculating means 65 and the transition data generating means 66 will be described. The index value calculating means 65 and the transition data generating means 66 calculate index values which are effective for diagnosis, and analyze temporal changes thereof. Commonly, index values which are effective for diagnosis differ for each body tissue. For this reason, the index value calculating means 65 and the transition data generating means 66 are equipped with a plurality of types of functions. The index value calculating means 65 and the transition data generating means 66 judge the type of body tissue which is the target of diagnosis, based on user operations or data recorded in the header regions of the files supplied thereto, and select processes to be executed.

Figure 9:
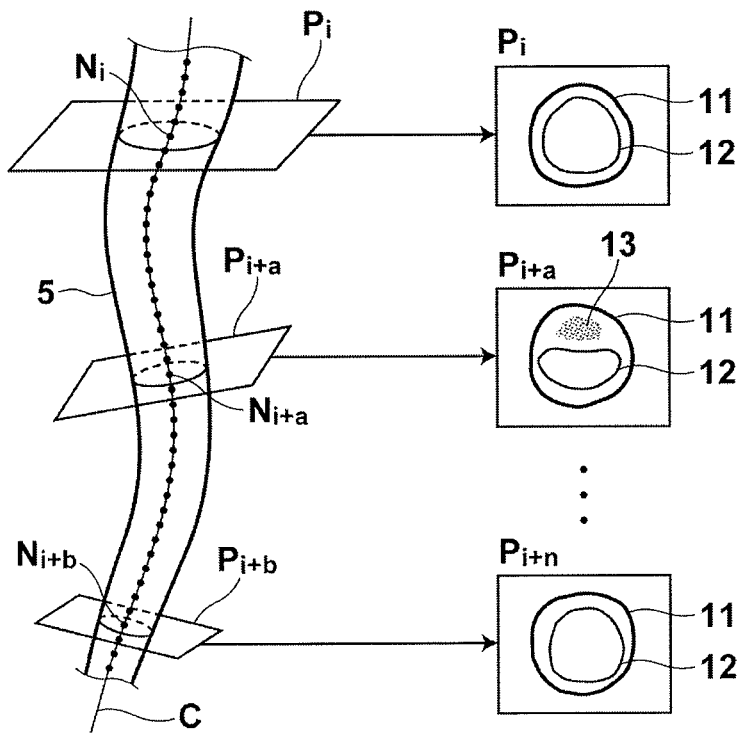
FIG. 9 is a diagram that illustrates an example of index values being calculated for each of a plurality of regions of interest (regarding stenosis rates of a blood vessel).

FIG. 9 illustrates a process executed by the index value calculating means 65 in the case that a function for assisting diagnosis of coronary arteries is selected. In the case that the function for assisting diagnosis of coronary arteries is selected, the index value calculating means 65 executes the following process with respect to each set of volume data V1 through V4. The index value calculating means 65 defines a cross section P for each candidate point N which is detected along the cores C during extraction of the coronary artery regions, for the set regions of interest. Then, analysis processes are executed for each cross section, to detect the outline of an inner cavity region 12. Further, the outline of a healthy inner cavity region 11 is estimated. Then, ratios of the areas of the region 12 and the region 11 are calculated, to derive rates of stenosis for the cross sections as an index value. In addition, soft plaque 13 which is adhered to the inner walls of blood vessels may be detected, and the percentage of the portions at which stenosis is present that the soft plaque 13 occupies may be calculated.

Figure 10:
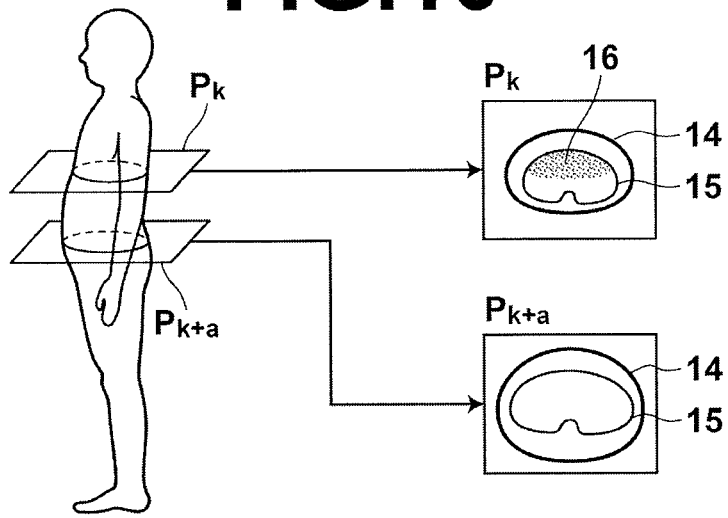
FIG. 10 is a diagram that illustrates an example of index values being calculated without setting regions of interest (regarding body fat percentage).

FIG. 10 illustrates a process executed by the index value calculating means 65 in the case that a fat measuring function is selected. In the case that the fat measuring function is selected, the index value calculating means 65 executes the following process with respect to each set of volume data V1 through V4. In the present embodiment, each cross section is analyzed by the observation target extracting means 62, and the outline 14 of the abdomen, the boundary line 15 of the inner side of the bone region, and the visceral fat region 16 have been detected. Accordingly, the index value calculating means 65 calculates the area of the visceral fat region within each cross section, and outputs the calculated areas as first index values. Further, the total volume of the visceral fat is derived by integrating the calculated areas within the plurality of cross sections, and output as a second index value. Still further, the area of the region surrounded by the outline 14 is calculated for each cross section, and the volume of the entire abdomen is derived by integrating the calculated areas. Then, a body fat percentage is derived by calculating the ratio of the volume of visceral fat and the volume of the abdomen, and output as a third index value.

One or a plurality of types of index values are obtained for each set of volume data by the processes exemplified above, and supplied to the transition data generating means 66.

The transition data generating means 66 arranges the index values calculated for each set of volume data by type and in chronological order, and derives amounts of transitions of the index values among examination dates, by calculating the differences between temporally adjacent index values. Further, values that represent the trends in transitions of the index values among examination dates, such as increases and decreases, are calculated based on the calculated differences. The values that represent the trends in transitions are not limited to rates of increase/decrease, but may be values that represent the increasing/decreasing trends. For example, a value of 1 may represent increases, a value of 0 may represent no change, and a value of −1 may represent decreases.

In the case that the index values are calculated for each region, and the regions at which transitions have occurred are not set as regions of interest, the transition data generating means 66 additionally sets such regions as new regions of interest. Data regarding the additionally set regions of interest are added to the snapshots.

The transition data generating means 66 generates transition data, which includes data regarding the types of index values in which transitions were detected, regions (slice positions, etc.) in which large transitions were detected, the calculated differences, and the rates of increase/decrease. The generated transition data are supplied to the map generating means 64 and the predicting means 67, as illustrated in FIG. 1.

Note that in the case that the index values are calculated for each region, it is necessary for differences to be obtained among index values which are calculated for the same regions. However, the sets of volume data included in the files F1 through F4 are data obtained on different examination dates. Therefore, there are cases in which the shapes of extracted regions partially differ, due to influence of respiration and changes in symptoms of disease. For example, between states in which a bump is present and in which a bump is not present on a coronary artery, the core line of the blood vessel shifts due to a difference in the thickness of the blood vessel, and there are cases in which different points are detected as candidate points. In these cases, the cross sections which are set with respect to the candidate points will differ among the sets of volume data.

However, substantially the same points are detected as the candidate points within regions at which temporal changes have not occurred. Therefore, the tree structures can be matched among sets of volume data (graph matching) by using the candidate points within regions at which changes do not occur over time. That is, the degrees of similarity for main nodes are calculated based on a predetermined evaluation function, and the candidate points having the highest degrees of similarity are correlated with each other. Then, the correspondent relationships among the other candidate points are estimated based on the correspondent relationships among the main nodes of the tree structure. By this method, points which are the same anatomically can be correlated with each other, even if the shapes of the coronary artery regions extracted from sets of volume data are different. Note that various other methods for correlating anatomic structures by graph matching have been proposed, as disclosed in U.S. Pat. No. 7,646,903. In the present embodiment, the nodes and cross sections are correlated to each other by executing such matching processes, and the differences and the like among index values of corresponding cross sections are calculated.

A positioning method that utilizes structures unique to the coronary arteries has been described above. However, the positioning may be performed by the method disclosed in U.S. Pat. No. 7,620,229, or by any other known method. In the present embodiment, the transition data generating means 66 is equipped with various types of positioning functions, and realizes accurate positioning, by selectively employing these functions according to the tissue which is the target of diagnosis.

Next, the map generating means 64 will be described. The map generating means 64 generates subject maps that include regions of interest, based on the sets of volume data and the snapshots output from the observation target extracting means 62, and the transition data supplied from the transition data generating means 66.

The subject maps are maps in which frames or marks that represent regions of interest are synthesized within volume rendering images and the like, which are generated from the sets of volume data obtained by imaging. Alternatively, the subject maps may be diagrams that represent only the outlines of the subjects, in which frames or marks are synthesized. As a further alternative, an image for observation may also function as a subject map, by synthesizing frames or marks therein.

As still another alternative, a method in which schema are generated utilizing the parameters saved in the snapshot and employed as the subject maps may be considered. For example, three dimensional data that represent a human anatomical model and a schema generating program that generates schema from a desired viewpoint and a desired field of view may be loaded in the diagnosis WS6. Then, the parameters which were employed to generate the images for observation from the sets of volume data may be read out from the snapshots, and the viewpoint and the field of view with respect to the human anatomical model may be determined based on the read out parameters. If the determined viewpoint and field of view are input to the schema generating program, a schema that represents an anatomical model of the organ which is the subject is generated from the same viewpoint and the same field of view as those of the images for observation. The schema which are generated in this manner have the advantage that they are schematic diagrams that facilitate understanding of positional display, and the advantage of images for observation that desired viewpoints and fields of view can be set. Therefore, such schema are suited for utilization as the subject maps.

As is clear from the examples described above, the subject map is not limited to any particular type of image or any generation method, as long as is enables instinctive understanding of regions at which transitions have occurred (regions of interest).

The display control means 68 displays data specified by predetermined user operations from among the index values calculated by the index value calculating means 65 and the transition data generated by the transition data generating means 66 to a history screen, along with the subject map generated by the map generating means 64. The specification of data is received via a selection menu or a predetermined setting screen. IN addition, in the case that the data specified by users contains a large amount of data and cannot be displayed within a single screen, the display control means 68 controls display such that only a portion of the data appears on the screen, and the remaining data appear on the screen when a scrolling operation or the like is performed.

The layout of the history screen differs according to the type of subject. However, all history screens are of layouts that enable understanding of the regions of interest and changes in the index values calculated for these regions, that is, the relationships among the history of examination results, at a single glance.

For example, the history screen 73 exemplified in FIG. 11A is a screen which is displayed when the function for assisting diagnosis of coronary arteries is selected, and the history button H is clicked in the diagnosis screen of FIG. 5A. An image of the blood vessel branches that constitute the coronary arteries and frames that indicate regions of interest ROI1, ROI2, and ROI3 are displayed as a subject map MAP on the left side of the history screen 73. Note that in the example of FIG. 11, the regions of interest are indicated by rectangular frames. Alternatively, the shapes of the frames may be circles or ovals. In addition, history windows 22a, 22b, and 22c that indicate histories of examination results for each of the regions of interest ROI1, ROI2, and ROI3 are displayed on the right side of the history screen 73.

In the present embodiment, the display control means 68 displays history windows of different formats, according to the type of subject, the types of index values, and the transition states of the index values. For example, the history windows 22a and 22b illustrated in FIG. 11A arrange the calculated index values in chronological order, to enable temporal changes in the regions of interest to be understood at a single glance.

Note that in the present embodiment, in the case that the number of examinations is great, a scroll bar appears underneath the history windows, and history that cannot be displayed within each single window is enabled to be displayed by performing scrolling operations. FIG. 11A illustrates a state in which a scroll bar 23 is displayed beneath the history window 22a.

In addition, the index values are not merely arranged in chronological order in the history window 22c, but a rate of increase/decrease calculated based on the difference in index values is also displayed. The example of FIG. 11A is that in which a rate of increase is 50%. In the case that the index value decreases by 50%, "50% decrease" will be displayed. Alternatively, the rate of increase may be displayed as 50%, and the rate of decrease may be displayed as −50%. As further alternatives, the amount of change, such as the amount of increase (2 mm$^2$) and the amount of decrease may be displayed instead of the rate of increase/decrease.

Figure 11B:
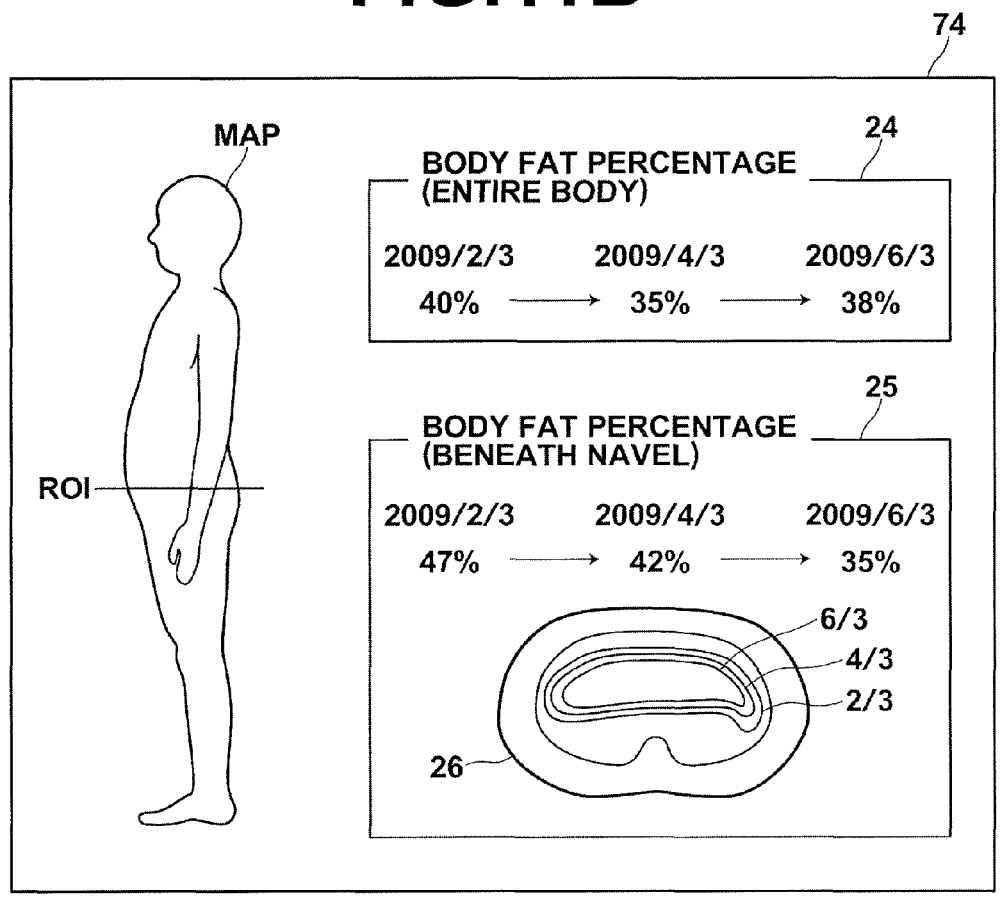
FIG. 11B is a diagram that illustrates another example of a history screen (in the case of fat measurement).

A history screen 74 exemplified in FIG. 11B is a screen which is displayed when the fat measuring function is selected, and the history button H is clicked in the diagnosis screen of FIG. 5B. A schematic image of a human body that indicates a slice position which has been set as a region of interest ROI is displayed as a subject map MAP at the left side of the history screen 74. In addition, a history window 24 that indicates transitions in body fat percentage of the entire abdomen and a history window 25 that indicates transitions in body fat percentage only with respect to the region of interest ROI, which is set below the navel, are displayed at the right side of the history screen 74. In addition to body fat percentages arranged in chronological order, an image 26, in which the outlines of visceral fat regions detected at each examination are overlapped on an orthogonal cross sectional image of the abdomen, is displayed in the history window 25.

Next, the predicting means 67 will be described. The predicting means 67 calculates the values of index values to be expected after a predetermined period of time (six months or a year, for example), based on the transition data generated by the transition data generating means 66. An example of a method for predicting future index values based only on the transition data is to calculate an annual average rate of increase from the values of rates of increase included in the transition data, and to estimate a value, which is a current value increased by the annual average rate of increase, as the index value to be expected one year later.

Figure 12:
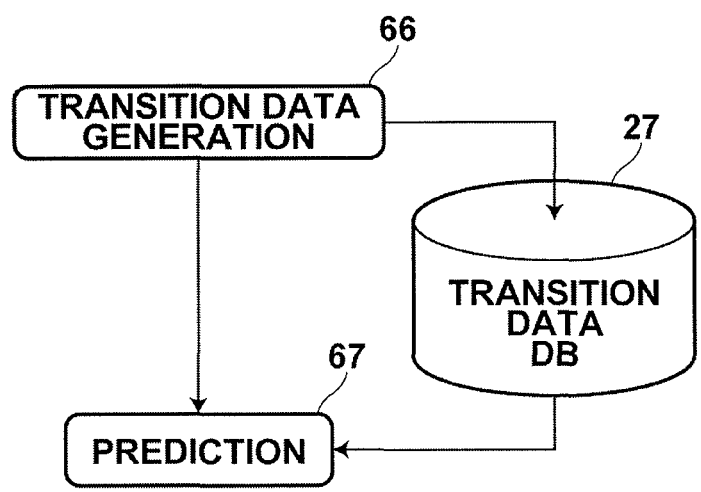
FIG. 12 is a diagram that illustrates an example of a system configuration in the case that prediction is performed.
Figure 13:
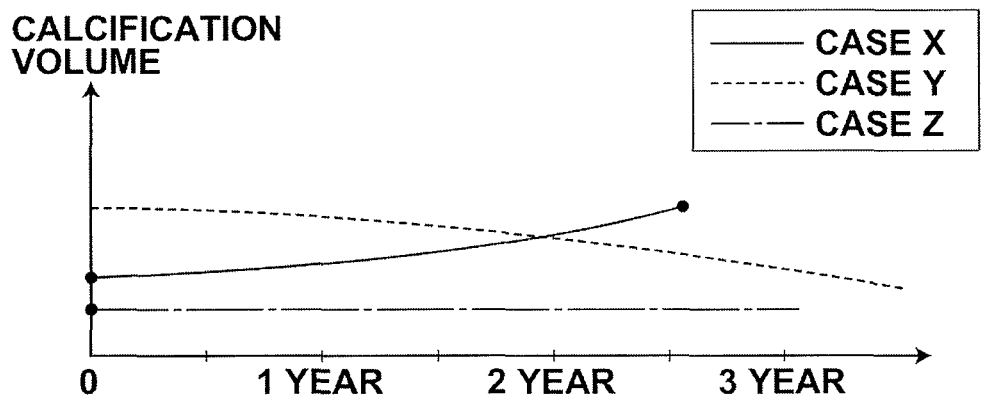
FIG. 13 is a diagram that illustrates an example of data which are registered in a transition data database.

However, trends in transitions are not necessarily uniform or constant. Therefore, the system of the present embodiment performs predictions by referring to data of medical cases having similar transition trends. Specifically, the system of the present embodiment accumulates and stores the transition data generated by the transition data generating means 66 in a manner correlated with electronic medical charts in which treatment histories are recorded, as illustrated in FIG. 12. The predicting means 67 searches for cases that have similar transition trends, by matching the transition data supplied from the transition data generating means 66 with the transition data of past cases which are accumulated in the database 27.

For example, if the transition data supplied by the transition data generating means 66 indicates substantially no change in the volume of a calcified region for a year, matching of transition data is performed for a period of one year from the point in time that the calcification region was detected. As a result, three cases X, Y, and Z are detected as past cases in which the volumes of calcified regions remained substantially the same for the first year. Assume that it is recorded that cases X and Z are cases that were left untreated, and case Y was treated with medication in the electronic medical charts associated with the transition data. In this case, the predicting means 67 calculates estimated index values two years from the most recent examination and three years from the most recent examination, for two cases, one in which the volume of the calcified region increases at the same rate as that of case X and one in which the volume of the calcified region decreases at the same rate as that of case Y.

When the prediction button F is clicked in the diagnosis screens exemplified in FIG. 5A and FIG. 5B, the display control means 68 displays the subject map generated by the map generating means 64, the index values calculated by the index value calculating means 65, the transition data generated by the transition data generating means 66, and the estimated index values calculated by the predicting means 67 on the prediction screen.

The layout of the prediction screen differs according to the type of subject. However, all prediction screens are of layouts that enable understanding of the regions of interest and changes in the index values calculated for these regions, that is, the relationships among the history of examination results, at a single glance.

Figure 14:
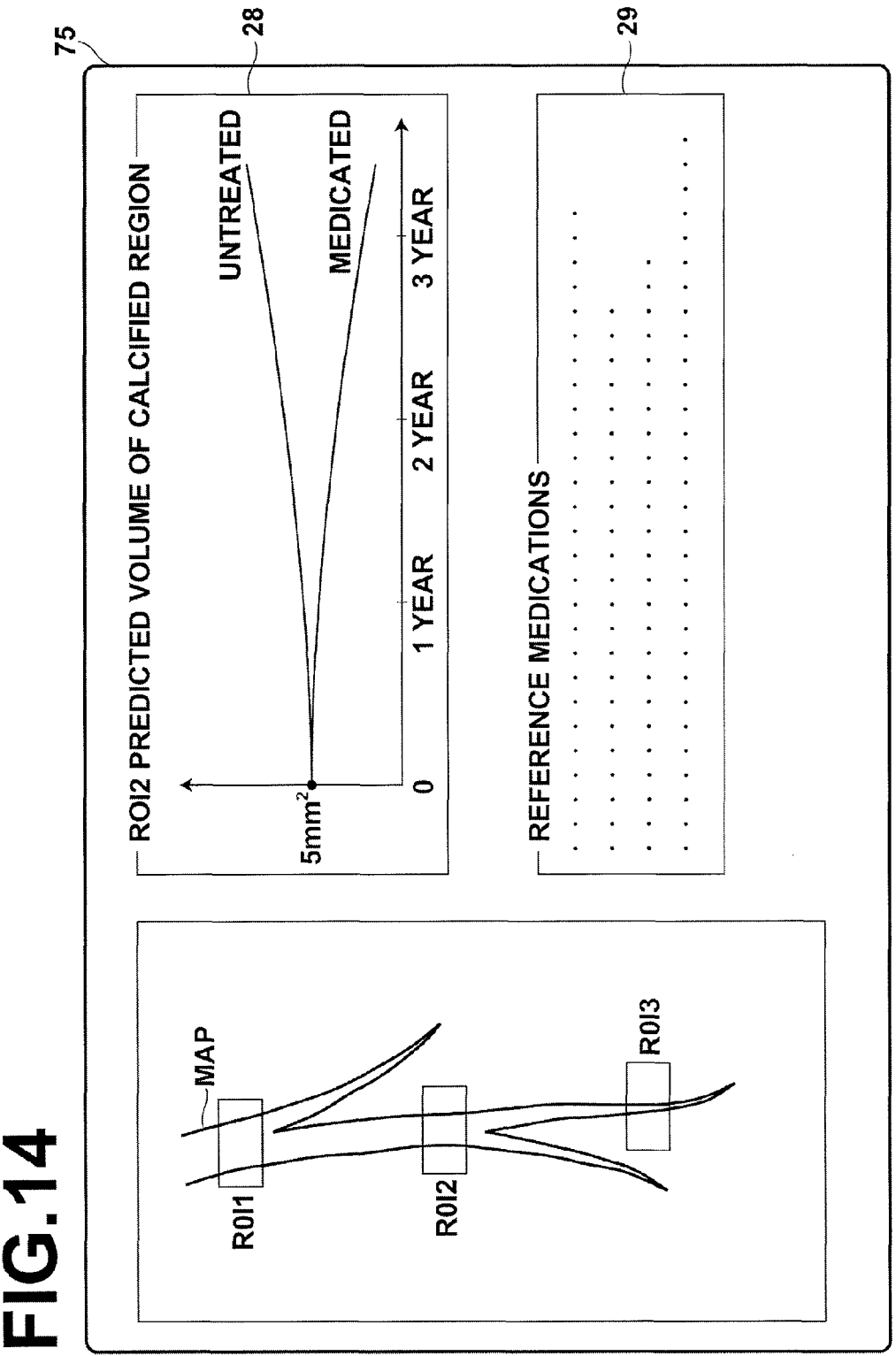
FIG. 14 is a diagram that illustrates an example of a prediction screen.

In the present embodiment, the prediction screen 75 exemplified in FIG. 14 is displayed in the case that prediction of the volume of calcified regions is performed as in the example described above. The same subject map as that displayed in the history screen is displayed at the left side of the prediction screen 75. A graph that indicates the estimated index values two and three years after the most recent examination for the two cases described above is displayed at the right side of the prediction screen 75. In addition, information regarding medications (types of medications, amounts, and period of treatment) read out from the electronic medical chart correlated to case Y is displayed as a reference for treatment with medication.

As described above, the present embodiment enables instantaneous understanding of temporal changes in the state of the subject by viewing the history screen, even in cases that repeated examinations are performed and a great number of sets of volume data have been accumulated and stored. The history screen is extremely effective when it is necessary to quickly and accurately understand progress to date, such as when treatment protocols are to be reconsidered and when attending physicians change.

Further, the present embodiment enables confirmation of estimated future states, by viewing the prediction screen. The index values and the like displayed on the prediction screen are values which are estimated based on past similar cases, and therefore, the accuracy of predictions is comparatively high. The display of the prediction screen is helpful when considering treatment protocols, and also as materials to explain treatment to patients.

Note that in the embodiment described above, the history screen and the prediction screen are displayed on a display different from those on which the diagnosis screens are displayed. Alternatively, a configuration may be considered, in which the history windows, etc. are displayed overlapped on a diagnosis screen that represents the oldest or the most recent examination results.

In addition, the layouts and the contents displayed in the history screen and the prediction screen are not limited to the examples described in the above embodiment, and other layouts and display contents may be adopted. For example, layouts in which the index values are displayed arranged in chronological order in the vicinities of regions of interest within subject maps, and in which rates of increase/decrease are displayed in the vicinities of regions of interest within subject maps may be considered.

In the embodiment described above, only one subject map is generated by the map generating means 64. Alternatively, a plurality of subject maps may be generated and displayed. For example, a first subject map that represents the entirety of the coronary arteries and a second subject map that represents a portion of blood vessel branches of the coronary arteries may be generated.

In this case, the position of the blood vessel branches represented by the second subject map within the coronary arteries as a whole may be indicated within the first subject map.

In the embodiment described above, the observation targets are extracted after the sets of volume data are selected. Alternatively, processes for extracting body tissue as targets of diagnosis, such as coronary artery regions and fat regions, may be performed by the examination room WS 31 of the examination room system 3, and only setting of the regions of interest may be performed after the sets of volume data are selected.

In the above description, cases in which a function for assisting diagnosis of coronary arteries and in which a fat measuring function are selected have been described. However, it is clear that the above method can be applied to construct a system that displays history screens and prediction screens that would be helpful to diagnosis of various types of body tissues, such as the head (brain), the lung field, the heart, the stomach, and the intestines.

The above embodiment has been described as a client/server system. Alternatively, a single computer may function as the volume data storage means, the volume data selecting means, the observation target extracting means, the observation image generating means, the map generating means, the index value calculating means, the transition data generating means, the predicting means, and the display control means. In addition, the processes performed by the diagnosis WS 6 in the embodiment described above may be divided among a plurality of computers and executed.

In FIG. 1, the observation image generating means and the map generating means are illustrated as separate means. However, a configuration may be adopted in which images for observation are utilized as subject maps, as described previously. In this case, the observation image generating means will be equipped with the functions of the map generating means.

With respect to devices that constitute the system, such as the input device and the display, various known devices may be employed. For example, a joystick may be substituted for the mouse, and a touch panel may be substituted for the display.

As described above, the present invention is not limited to the embodiment described above. Various changes and modifications are possible, as long as they do not stray from the spirit of the invention. In addition, the present invention is not limited to assisting diagnosis of coronary arteries, and may be employed to assist diagnosis of various living tissue. Further, the present invention is not limited to assisting diagnosis of living organisms, and may be utilized for periodic inspections to assess deterioration of machinery and the like.

What is claimed is:

1. A diagnosis assisting system, comprising:
   volume data storage means, for storing a plurality of sets of volume data, obtained by imaging at least one subject on different imaging dates/times, in a predetermined storage device, correlated with subject identifying data and imaging date or time data;
   volume data selecting means, for selecting a plurality of sets of volume data correlated with subject identifying data that represents a specified subject, from among the sets of volume data stored in the storage device;
   index value calculating means, for calculating at least one type of index value that represents the state of the subject within each set of volume data, by analyzing the selected plurality of sets of volume data;
   transition data generating means, for generating transition data that represent temporal transitions in the index values for each type of index value, based on the index values calculated for each set of volume data;
   map generating means, for generating at least one subject map that includes regions in which transitions are detected, by employing the transition data and at least one of the selected sets of volume data;
   predicting means, for calculating index values that present the future states of the subjects, based on the transition data;
   transition data storage means, for storing the transition data with respect to a plurality of subjects; and
   display control means, for outputting data specified by predetermined operations from among the index values calculated by the index value calculating means and the transition data generated by the transition data generating means to a predetermined screen, correlated with the regions on the at least one subject map at which the transitions have been detected,
   wherein the predicting means searches for at least one case of transition data similar to that the transition data generated by the transition data generating means, from among cases of the transition data stored in the transition data storage means, and calculates the index value that represents the future state of the subject using the transition rate of the index of the detected case of transition data, and
   wherein the display control means outputs the index values calculated by the predicting means, correlated with the regions on the at least one subject map at which the transitions have been detected.

2. A diagnosis assisting system as defined in claim 1, further comprising:
   region of interest setting means, for setting at least one region of interest within each of the selected sets of volume data; and wherein:
   the index value calculating means outputs index values that represent the states of the regions of interest, with respect to the at least one region so interest which has been set in one of the sets of volume data.

3. A computer readable non transitory recording medium storing a diagnosis assisting computer program, the computer program, when executed on at least one computer, causing the computer to perform a diagnosis assisting method, comprising the steps of:
   storing a plurality of sets of volume data, obtained by imaging at least one subject on different imaging dates/times, in a predetermined storage device, correlated with subject identifying data and imaging date or time data;
   selecting a plurality of sets of volume data correlated with subject identifying data that represents a specified subject, from among the sets of volume data stored in the storage device;
   calculating at least one type of index value that represents the state of the subject within each set of volume data, by analyzing the selected plurality of sets of volume data;
   generating transition data that represent temporal transitions in the index values for each type of index value, based on the index values calculated for each set of volume data;
   generating at least one subject map that includes regions in which transitions are detected, by employing the transition data and at least one of the selected sets of volume data;
   outputting data specified by predetermined operations from among the calculated index values and the generated transition data to a predetermined screen, correlated with the regions on the at least one subject map at which the transitions have been detected;
   calculating index values that represent the future states of the subjects, based on the transition data; and
   outputting said calculated index values that represent the future states of the subjects, correlated with the regions of the at least one subject map at which transitions have been detected, storing the transition data with respect to a plurality of subjects, and searching for at least one case of the transition data that has a transition trend similar to that of said generated transition data, from among cases of the stored transition data and calculating the index value that represents the future state of the subject using the transition rate of the index of the detected case of transition data.

4. A recording medium as defined in claim 3, wherein the computer further performs the functions of:
    setting at least one region of interest within each of the selected sets of volume data; and
    outputting index values that represent the states of the regions of interest, with respect to the at least one region so interest which has been set in one of the sets of volume data.

5. A diagnosis assisting method to be executed by at least one computer, comprising the steps of:
    storing a plurality of sets of volume data, obtained by imaging at least one subject on different imaging dates/times, in a predetermined storage device, correlated with subject identifying data and imaging date or time data;
    selecting a plurality of sets of volume data correlated with subject identifying data that represents a specified subject, from among the sets of volume data stored in the storage device;
    calculating at least one type of index value that represents the state of the subject within each set of volume data, by analyzing the selected plurality of sets of volume data;
    generating transition data that represent temporal transitions in the index values for each type of index value, based on the index values calculated for each set of volume data;
    generating at least one subject map that includes regions in which transitions are detected, by employing the transition data and at least one of the selected sets of volume data;
    outputting data specified by predetermined operations from among the calculated index values and the generated transition data to a predetermined screen, correlated with the regions on the at least one subject map at which the transitions have been detected;
    calculating index values that represent the future states of the subjects, based on the transition data; and
    outputting said calculated index values that represent the future states of the subjects, correlated with the regions of the at least one subject map at which the transitions have been detected, storing the transitions data with respect to a plurality of subjects, and searching for at least one case of the transition data that has a transition trend similar to that of said generated transition data, from among cases of the stored transition data and calculating the index value that represents the future state of the subject using the transition rate of the index of the detected case of transition data.

6. A diagnosis assisting method as defined in claim 5, wherein the computer further performs the functions of:
    setting at least one region of interest within each of the selected sets of volume data; and
    outputting index values that represent the states of the regions of interest, with respect to the at least one region so interest which has been set in one of the sets of volume data.

* * * * *